(12) United States Patent
Styrc

(10) Patent No.: US 7,648,528 B2
(45) Date of Patent: Jan. 19, 2010

(54) VALVE PROSTHESIS

(75) Inventor: Mikolaj Witold Styrc, Kopstal (LU)

(73) Assignee: Laboratoires Perouse, Ivry le Temple (FR)

( * ) Notice: Subject to any disclaimer, the term of this patent is extended or adjusted under 35 U.S.C. 154(b) by 242 days.

(21) Appl. No.: 11/661,940

(22) PCT Filed: Sep. 7, 2005

(86) PCT No.: PCT/FR2005/002228

§ 371 (c)(1),
(2), (4) Date: Mar. 6, 2007

(87) PCT Pub. No.: WO2006/027499

PCT Pub. Date: Mar. 16, 2006

(65) Prior Publication Data
US 2008/0077234 A1 Mar. 27, 2008

(30) Foreign Application Priority Data
Sep. 7, 2004 (FR) .................... 04 09469

(51) Int. Cl.
*A61F 2/06* (2006.01)
(52) U.S. Cl. .................................. 623/2.11
(58) Field of Classification Search .......... 623/2.1–2.19
See application file for complete search history.

(56) References Cited
U.S. PATENT DOCUMENTS

| | | | |
|---|---|---|---|
| 4,680,031 A | 7/1987 | Alonso | |
| 4,759,758 A * | 7/1988 | Gabbay | 623/2.13 |
| 4,790,843 A | 12/1988 | Carpentier et al. | |
| 5,163,955 A * | 11/1992 | Love et al. | 623/2.15 |
| 6,652,578 B2 | 11/2003 | Bailey et al. | |
| 6,730,121 B2 * | 5/2004 | Ortiz et al. | 623/2.17 |
| 7,101,396 B2 * | 9/2006 | Artof et al. | 623/2.18 |
| 7,267,686 B2 * | 9/2007 | DiMatteo et al. | 623/1.24 |
| 7,429,269 B2 * | 9/2008 | Schwammenthal et al. | 623/2.14 |
| 7,442,204 B2 * | 10/2008 | Schwammenthal et al. | 623/1.24 |
| 7,470,285 B2 * | 12/2008 | Nugent et al. | 623/2.18 |
| 2003/0040792 A1 * | 2/2003 | Gabbay | 623/2.11 |
| 2003/0125793 A1 | 7/2003 | Vesely | |
| 2003/0153974 A1 * | 8/2003 | Spenser et al. | 623/2.11 |
| 2008/0275540 A1 * | 11/2008 | Wen | 623/1.26 |
| 2009/0012600 A1 * | 1/2009 | Styrc et al. | 623/1.24 |
| 2009/0192599 A1 * | 7/2009 | Lane et al. | 623/2.4 |

FOREIGN PATENT DOCUMENTS

FR 2 847 800 6/2004

* cited by examiner

*Primary Examiner*—Suzette J Gherbi
(74) *Attorney, Agent, or Firm*—Wenderoth, Lind & Ponack, L.L.P.

(57) ABSTRACT

A valve prosthesis includes a flexible plug and an annular bearing reinforcement which is embodied such that it is radially rigid and surgically implantable in the area of a heart valve. The valve prosthesis is provided with an interchangeable prosthetic valve, is independent of the bearing reinforcement, endoluminally placeable and includes a tubular support which is radially deformable between a folded setting position and an unfolded position for implanting into a bearing structure and the flexible plug connected to a tubular support. The bearing reinforcement forms an annular support devoid of any plug capable of univocally limiting a blood flow circulation.

14 Claims, 5 Drawing Sheets

VALVE PROSTHESIS

BACKGROUND OF THE INVENTION

The present invention relates to a valve prosthesis to be put into place by an endoluminal approach. The prosthesis is the type comprising a flexible shutter and an annular carrier structure that is radially rigid and suitable for being surgically implanted at the location of a heart valve.

The heart comprises two atriums and two ventricles which are separated by valves. Valves are also present at the outlets from the right ventricle (pulmonary valve) and from the left ventricle (aortic valve).

These valves ensure that blood flows in one direction only, avoiding reflux of blood at the end of ventricular contraction.

Valves can suffer diseases. In particular, they can suffer from poor opening, thus reducing the flow of blood, or from being somewhat leaky, thus allowing a reflux or regurgitation of blood back into the ventricle that has just expelled it.

These regurgitation problems lead to abnormal expansion of the ventricle thereby producing, in the long run, heart failure.

It is known to treat that type of disease surgically, by replacing the diseased valve. Diseased valves, and in particular the aortic valve at the outlet from the left ventricle, are replaced by valves taken from a deceased subject, or by prosthetic valves, commonly referred to as bioprostheses. A prosthetic valve is constituted by a metal ring structure and a flexible shutter made of tissue of animal origin. The shutter is permanently secured to the structure.

Such valves are described in particular in documents WO 01/03095 and WO 00/27975.

Once implanted, the structure bears against the inside wall of the heart to which it is sutured, in particular at the inlet to the aortic valve coming from the left ventricle.

It is found that after such a prosthesis has been implanted for several years, it degenerates and no longer functions efficiently. In particular, the flexible shutter tears and presents holes, or the shutter becomes calcified and thus loses flexibility, thus no longer being capable of deforming to perform its valve function. It is then necessary to put a new prosthesis into place.

However, it is not possible to remove the old prosthesis via an endoluminal path, in particular because the carrier structure of the prosthesis is sutured to the wall of the heart, meaning that they cannot be separated without major surgery for complete replacement of the valve.

In order to avoid a major surgical operation for removing the old prosthesis and putting a second prosthesis into place, it has been envisaged that a new prosthetic valve could be put into place by an endoluminal approach inside the old prosthesis which is left in place.

The new prosthetic valve is formed by a tubular support constituted by a radially deformable lattice fitted with a flexible shutter disposed in the duct defined by the tubular support. The shutter is connected to the tubular support and presents a shape that enables it, by deforming, to allow blood to flow in one direction and to prevent the blood from flowing in the opposite direction.

It has been envisaged that the tubular support could be made of interlaced resilient metal wires defining meshes that are generally lozenge-shaped. Such a tubular support is known as a "stent". The tubular support is deformable between an insertion position, in which its diameter is reduced, and an implantation position in which its diameter is larger and sufficient to enable the support to bear against the inside of the carrier structure of the old prosthesis.

In order to be put into place, such prosthetic valves comprising a tubular lattice support are disposed inside a small-diameter catheter. The end of the catheter is brought via the arterial network to the region where the no longer functioning, old prosthesis has been fitted. The new prosthetic valve is pushed out from the catheter using a wire-shaped member engaged in the catheter. Since the tubular support is resilient, it deploys immediately on its own when it is no longer compressed radially by the catheter. It then comes to bear around the inside perimeter of the carrier structure of the old prosthesis.

Putting the new valve into place and deploying it are operations that are very difficult, particularly when the old prosthesis is very damaged.

SUMMARY OF THE INVENTION

An object of the invention is to propose a valve prosthesis that can be put back into condition easily by means of an endoluminal approach.

To this end, the invention provides a valve prosthesis of the above-specified type, which comprises:

an interchangeable prosthetic valve independent of the carrier structure to be put into place by an endoluminal approach through the annular carrier structure and comprising: a tubular support that is radially deformable relative to a main axis between a folded position for being put into place, and a deployed position implanted in the carrier structure, in which the tubular support bears at its periphery against the carrier structure.

The flexible shutter is connected to the tubular support and deformable between an obstruction position in which it is extended transversally and a release position in which it is contracted transversally under the action of the blood flowing through the tubular support.

The carrier structure forms an annular support having no shutter suitable for restricting the flow of blood to one direction only.

In particular embodiments, the valve prosthesis includes one or more of the following characteristics:

the tubular support defines a solid cylindrical wall that is liquid-proof;

the tubular support comprises a tubular lattice covered in a stretchable film that is liquid-proof and that forms the solid cylindrical wall;

The prosthesis includes at least one rigid member extending generally along a generator line of the tubular support, which member is connected to the tubular support at least two points that are spaced apart along the axis of the tubular support;

the tubular support presents a generally cylindrical middle trunk and, axially at either end of the trunk, two generally frustoconical collars flaring from the trunk towards the ends of the support;

the tubular support is resilient and is shaped to be urged resiliently from its folded position towards its deployed position;

each member has a projecting end for connection to a prop for holding the prosthetic valve in position;

the tubular support is extended by converging legs forming a tripod, which legs are connected together at a connection point lying substantially on the axis of the tubular support;

the shutter comprises three membranes that are deformable between a closed position in which the free edges of the membranes, over half their length, touch one another in pairs, and an open position for passing blood in which the three membranes are spaced apart from one another;

the carrier structure comprises a rigid ring and a set of rigid pegs each extending from the ring parallel to the axis of the ring; and the carrier structure includes at its surface a textile sheet making suturing possible.

The invention also provides a treatment kit comprising:

a valve prosthesis as described above; and a catheter for putting the prosthetic valve into place.

BRIEF DESCRIPTION OF THE DRAWINGS

The invention can be better understood upon reading the following description given purely by way of example and made with reference to the drawings, in which.

DETAILED DESCRIPTION OF THE INVENTION

Figure 1:
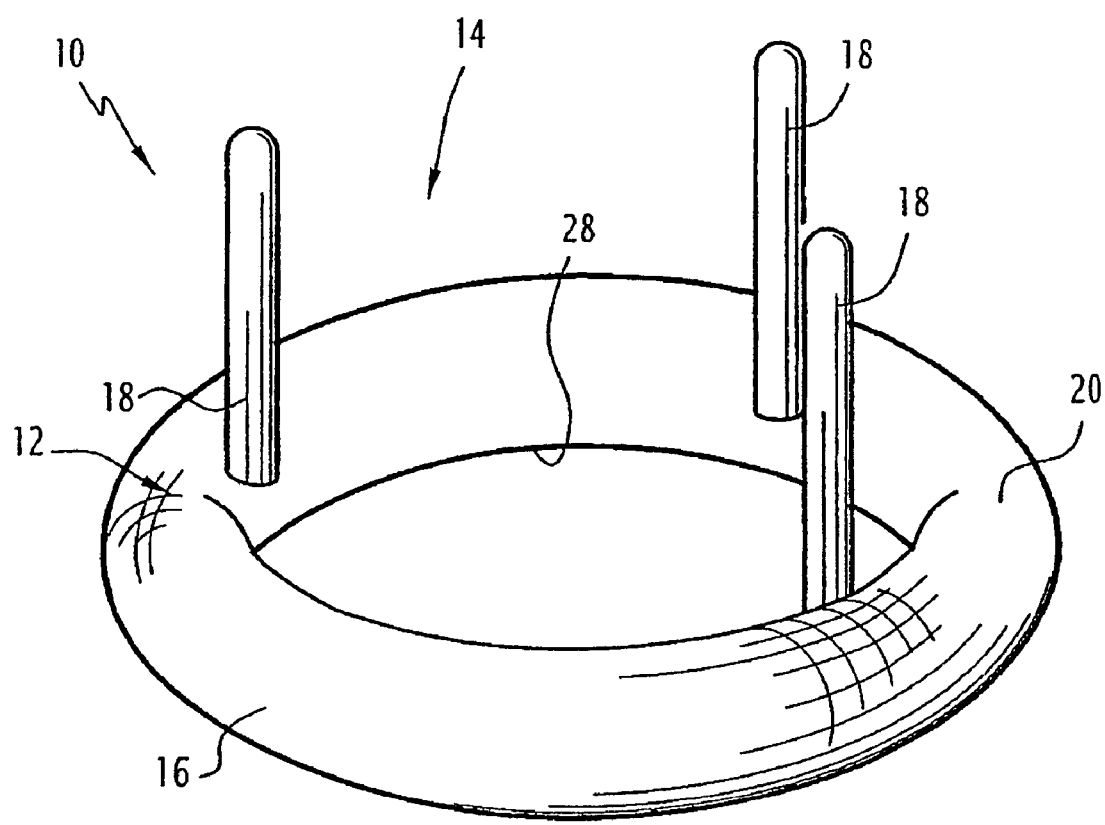
FIG. 1 is a perspective view of the carrier structure on its own of the valve prosthesis that is implanted surgically.
Figure 2:
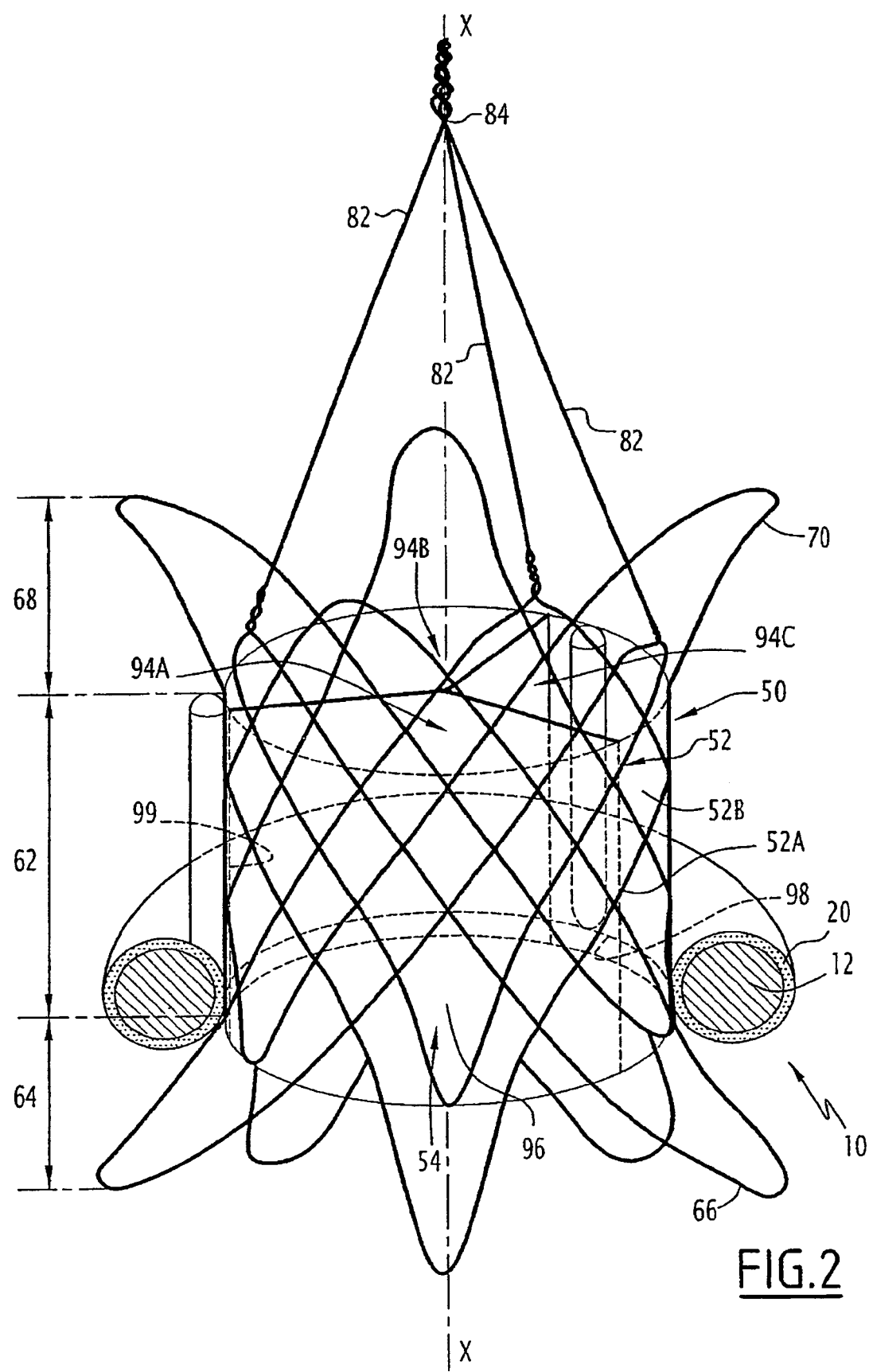
FIG. 2 is a perspective view of a valve prosthesis of the invention in its closed state.

In FIGS. 1 and 2, a valve prosthesis 10 that can be seen in full in FIG. 2 and only in part in FIG. 1. The valve prosthesis is for an aortic valve of the heart. Thus, this prosthesis is placed immediately upstream from the aorta at the location of the natural valve.

The valve prosthesis includes a carrier structure 12 that can be seen on its own in FIG. 1. This structure essentially comprises a rigid ring 16 carrying three rigid pegs 18, each extending from the ring parallel to the axis of the ring 16. This ring is constituted by a rigid metal torus having the three pegs 18 welded thereto. The torus is covered over its entire surface in a woven textile sheet 20 enabling the carrier structure to be secured to the tissue of the heart by suturing the textile sheet to the wall of the heart. The inside diameter of the ring 16 lies in the range 15 millimeters (mm) to 40 mm.

Each peg 18 has one end secured to ring 16, and all of them project from the same side of the ring. They are regularly distributed (evenly spaced) angularly around the axis of the carrier structure 12. The total height of the pegs 18, including the ring 16, lies in the range 10 mm to 30 mm.

The carrier structure 12 does not have any flexible shutter deformable in the space defined by the structure between a closed position and an open position.

FIG. 2 shows a valve prosthesis 10 of the invention after it has been implanted. The valve prosthesis comprises, in addition to the carrier structure 12, a prosthetic valve 50 that is interchangeable by an endoluminal approach. In the implanted state, the prosthetic valve extends inside the carrier structure 12 that has previously been implanted surgically.

The prosthetic valve 50 comprises a lattice tubular support 52 of axis X-X and a flexible shutter 54 connected to the tubular support 52 and placed inside it.

The valve 50 is replaceable and is normally removable relative to the carrier structure 12.

The tubular support 52 is constituted, for example, by a tubular lattice 52A embedded in a stretchable film 52B that is liquid-proof, such as an elastomer. Since the film 52B covers the lattice, it defines, over the entire height of the support 52, a cylindrical wall that is solid and liquid-proof. The lattice 52A is made of stainless steel having elastic properties, such that the support 52 is self-expanding. Such a support, when used on its own, is commonly referred to as a "stent".

As is known, the support 52 can deform spontaneously from a compressed state in which it presents a small diameter to a dilated state in which it presents a diameter that is greater, the dilated state constituting its rest state.

Figure 3:
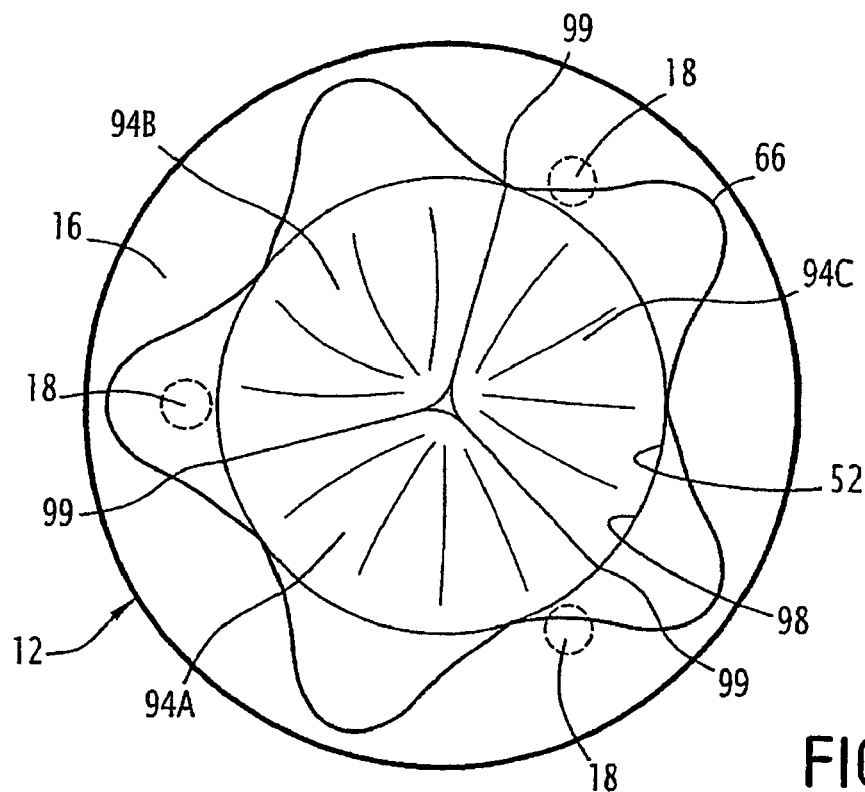
FIG. 3 is an end view of the FIG. 2 valve prosthesis.
Figure 4:
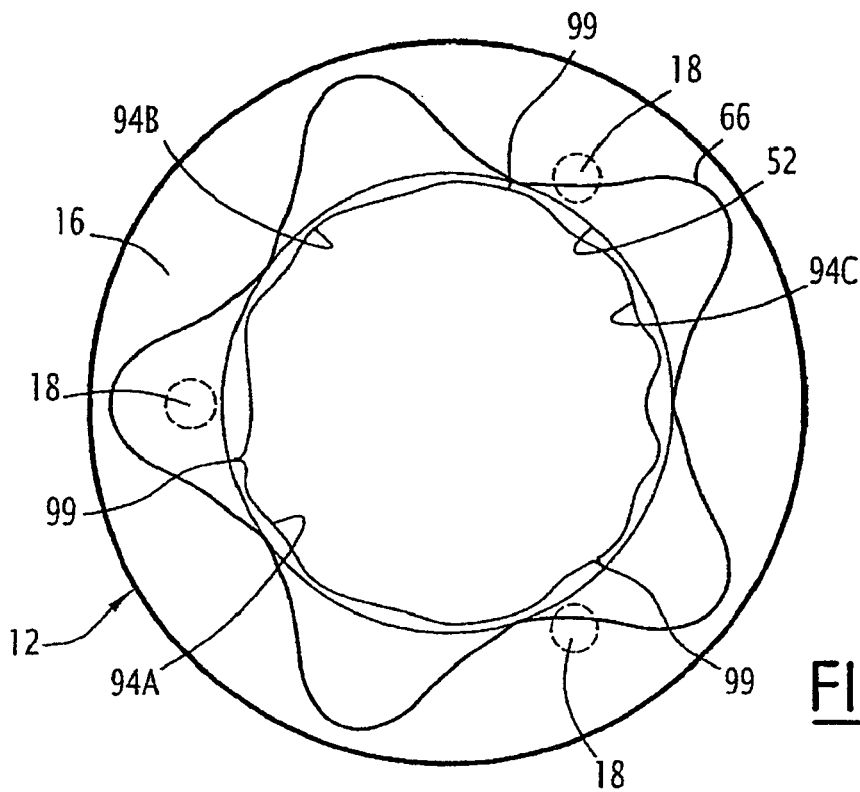
FIG. 4 is a view identical to that of FIG. 3, the valve prosthesis being in its open state.

In its implanted state, as shown in FIGS. 2 to 4 and because of its resilience, the support 52 bears against the ring 16 and the pegs 18 of the valve prosthesis 10, holding the three pegs 18 pressed against the outside surface of the support 52.

At each of its axial ends, the support 52 extends axially beyond the carrier structure by two diverging collars that are generally truncated in shape, flaring towards the axial ends of the support.

More precisely, the support 52 has a middle trunk 62 that is generally cylindrical, of a length corresponding to the height of the carrier structure, this height being measured along the axis of the valve. The height of the trunk lies in the range of 10 mm to 30 mm.

The lattice defining the trunk 62 is made up of interlaced metal wires. Thus, two families of wires cross over one another. The wires in the first family define helixes oriented in the same direction and extending generally parallel to one another. The wires of the second family define helixes oriented in the opposite direction and extending parallel to one another. The wires of the first and second families are engaged successively over and under one another, such that these families of wires define lozenge-shaped meshes, with one diagonal of each mesh extending along the axis of the support, and with its other diagonal extending generally perpendicularly.

At a first end of the support, the trunk 62 is extended by a first flared collar 64 constituted by a set of lobes 66 going away from the axis of the support towards their curved ends. These lobes are formed by loops made at the ends of the wires of the first and second families, and they are integral therewith.

Similarly, at its other end, the support has a second flared collar 68 extending the trunk 62. This second collar is likewise defined by outwardly-deformed lobes 70.

At rest, the free ends of the collars, i.e. the most highly-flared end sections of the collars, define an outline of diameter equal to the diameter of the trunk 62 plus 5 mm to 15 mm.

Similarly, and advantageously, the height of the collars 64, 68, measured along the axis of the tubular support 52 lies in the range of 5 mm to 15 mm, and for example is equal to 10 mm.

The film 52B in which the tubular lattice 52A is embedded extends over the lobes forming the collars 64 and 68.

In a first embodiment, the tubular support 52 has over its entire height while at rest, i.e. when it is not compressed in a structure 12, a diameter that is greater than the diameter of the structure 12, such that the collars 64 and 68 take up a flared shape merely because of the natural resilience of the tubular support while the trunk is kept confined in a tubular shape within the carrier structure 12.

In a variant, the trunk 62 of the tubular support, when at rest, and even when not compressed inside a structure 12, has a diameter that is smaller than the end diameter of the collars 64 and 68.

Furthermore, three pairs of wires coming from the first and second families respectively are connected together in pairs at the collar 68 to form three legs 82. The legs converge towards one another along the axis X-X of the prosthetic valve in order to meet at a connection point 84 located on the axis. The three legs 82 thus define a tripod. They are regularly distributed (evenly shaped) angularly around the axis X-X, and each of them defines relative to the axis an angle that lies in the range 20° to 40°. For connection purposes, the three legs 82 are, for example, twisted together at the point 84. A connection loop is made at the end point 84.

In addition, and according to the invention, the tubular support 52 includes at least one rigid member 90 extending generally along a generator line of the tubular support 52. This member is connected to the support at least at two points 92A, 92B that are spaced apart along the axis of the support. These two points are formed along the height of the trunk 62, in particular in the vicinity of the regions where it connects with the collars 64 and 68. Connection may be performed by welding or by adhesive bonding.

Advantageously, a single rigid member 90 is formed along one generator line of the trunk 62. By way of example, this member is constituted by a longitudinally rigid metal wire that is engaged through the meshes of the lattice, passing alternately inside and outside the lattice.

Advantageously, the ends of the member are disposed inside the tubular support, i.e. beside the axis X-X relative to the liquid-proof film 52B.

Figure 5:
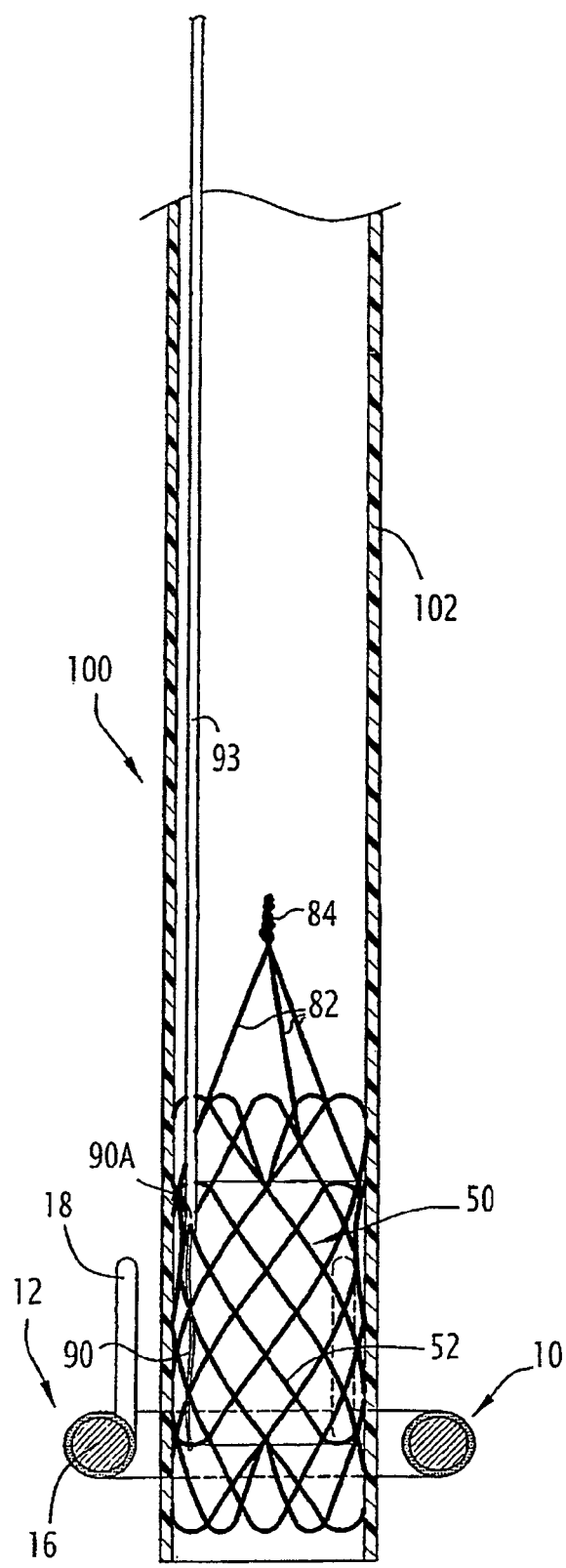
FIGS. 5 and 6 are longitudinal section views showing the successive stages in putting a prosthetic valve of a valve prosthesis of the invention into place.

At least one projecting end 90A of the member 90, and in particular its end adjacent to the legs 82, is suitable for cooperating with a prop 93 for axial connection therewith, as shown in FIG. 5 and as explained below. The axial connection between the prop 93 and the member 90 is provided, by way of example, by the connection end 90A of the member being engaged in a housing provided in the thickness of the prop 93 and opening out in the end thereof.

The shutter 54 is connected to the inside surface of the tubular support 52. This shutter is made up of three flexible membranes 94A, 94B, and 94C, each constituted by a polymer film or a layer of organic film such as calf pericardium. Each membrane is generally rectangular in shape. It is connected to the inside surface of the liquid-proof film 52B along a base-forming long side 98 around the connection circumference between the trunk 62 and the enlarged collar 64.

The longitudinal edges 99 of the three membranes 94A, 94B, and 94C are connected to the tubular support 52 along three generator lines thereof that are regularly distributed angularly around the axis of the tubular support. Thus, the membranes are connected in pairs along their longitudinal edges to the tubular support. This connection is performed over the entire height of the trunk 62.

The shutter-forming membranes 94A, 94B, and 94C are deformable between a closed position shown in FIGS. 2 and 3 in which the free edges of the membranes touch one another in pairs along half of their length, and a position for passing blood, as shown in FIG. 4 in which the three membranes are moved apart from one another.

In the closed position, the three membranes cooperate with the tubular wall of the support 52 to define three pouches for retaining the stream of blood. In the open position, the three membranes are pressed against the inside surface of the tubular support, as shown in FIG. 4, thus together defining a generally circular duct in which the stream of blood can flow.

When the valve prosthesis is put into place initially, the surgeon begins by putting the carrier structure 12 into place by a surgical approach. For this purpose, an incision is made in the patient's chest to bring the carrier structure 12 to the heart, where it is implanted to take the place of the original valve. The carrier structure 12 is secured to the wall of the heart by sutures engaged in the textile coating 20 of the ring.

During initial implanting of the valve prosthesis, the prosthetic valve 50 is put into place manually inside the carrier structure 12, after which the patient's chest is sewn back up.

The structure 12 is implanted permanently in the patient's body, while the prosthetic valve 50 is interchangeable. Thus, when the prosthetic valve 50 becomes damaged (in particular, because the membranes have become calcified or torn), the prosthetic valve is extracted by an endoluminal approach as explained below, and the new prosthetic valve is put into place in the space defined by the carrier structure 12, as explained below.

Figure 6:
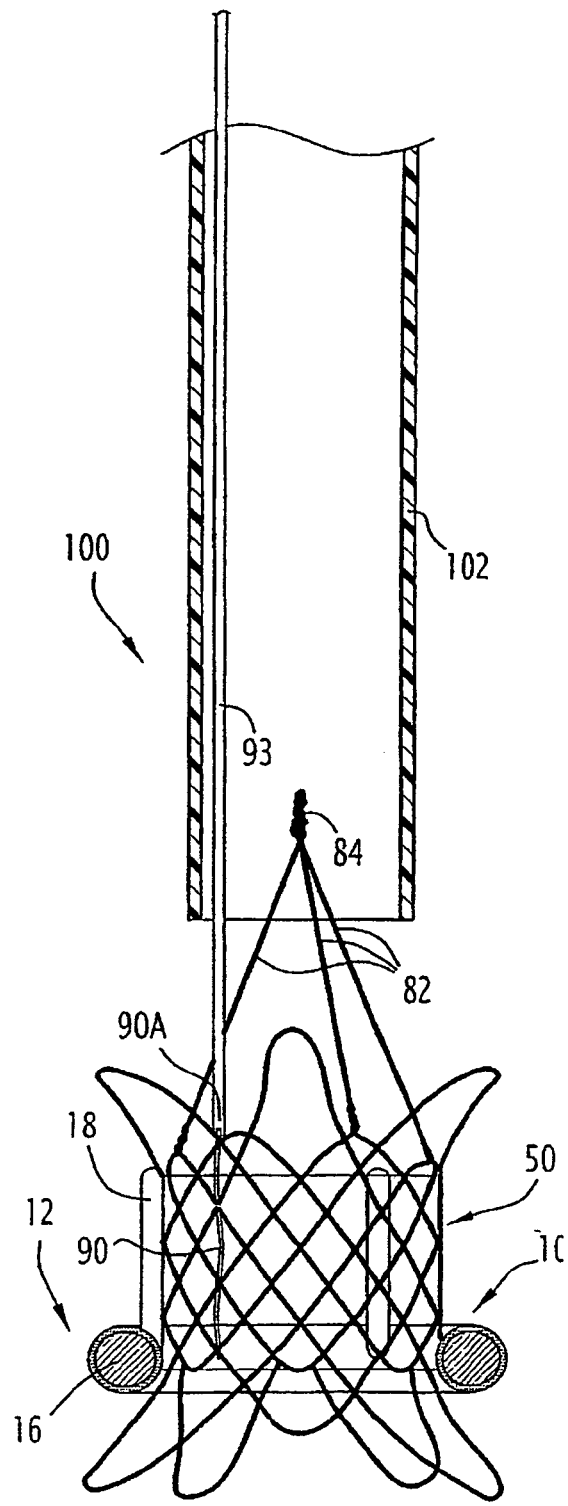

To put a new prosthetic valve 50 in place by an endoluminal approach, a treatment kit 100, shown in FIGS. 5 and 6, is used. It comprises a new prosthetic valve 50 contained in a catheter 102 of outside diameter smaller than the inside diameter of the carrier structure 12.

As shown in FIG. 5, the prosthetic valve, and in particular the tubular support 52, is compressed radially inside the tube.

In addition, the prop 93 extends lengthwise along the catheter 102 being connected at its end to the end of the axial stiffener (rigid) member 90. The prop 93 has sufficient axial stiffness to be capable of pushing the prosthetic valve out from the catheter 102.

During installation of the valve, the end of the catheter 102 in which the prosthetic valve is received is inserted in the patient's aorta, and is then moved progressively along the aorta to the location of the damaged prosthetic valve at the outlet from the heart. The catheter is moved against the normal flow of blood.

The catheter is brought into the position shown in FIG. 5. In this position, the catheter 102 is then pulled while the new prosthetic valve 50 is held in place by the prop 93. As the catheter 102 moves, the prosthetic valve 50 becomes uncovered, such that its first end deploys to form the collar 64, and then the tubular support trunk 62 comes to bear against the pegs 18, and finally its second end deploys to form the collar 68.

During the progressive baring of the prosthetic valve 50 by moving the catheter 102, the prosthetic valve is held stationary in an axial direction relative to the ducts of the aorta, and in particular relative to the carrier structure 12 left in place by means of the rigid prop 93 which holds the member 90 in line therewith. Thus, the presence of the prop 93 cooperating with the member 90 reduces the risk of the prosthetic valve moving axially as it is being deployed, even if it is deployed during a heartbeat causing blood to flow through the location of the valve.

After deployment, the valve is held axially by the presence of the enlarged collars 64 and 68 bearing respectively on the ring 16 and on the ends of the pegs 18.

After deployment, the prop 93 is withdrawn merely by traction. Thus, the member 90 disengages from the end of the prop 93. The member 90 remains in position since it is integrated in the tubular support 52.

Figure 7:
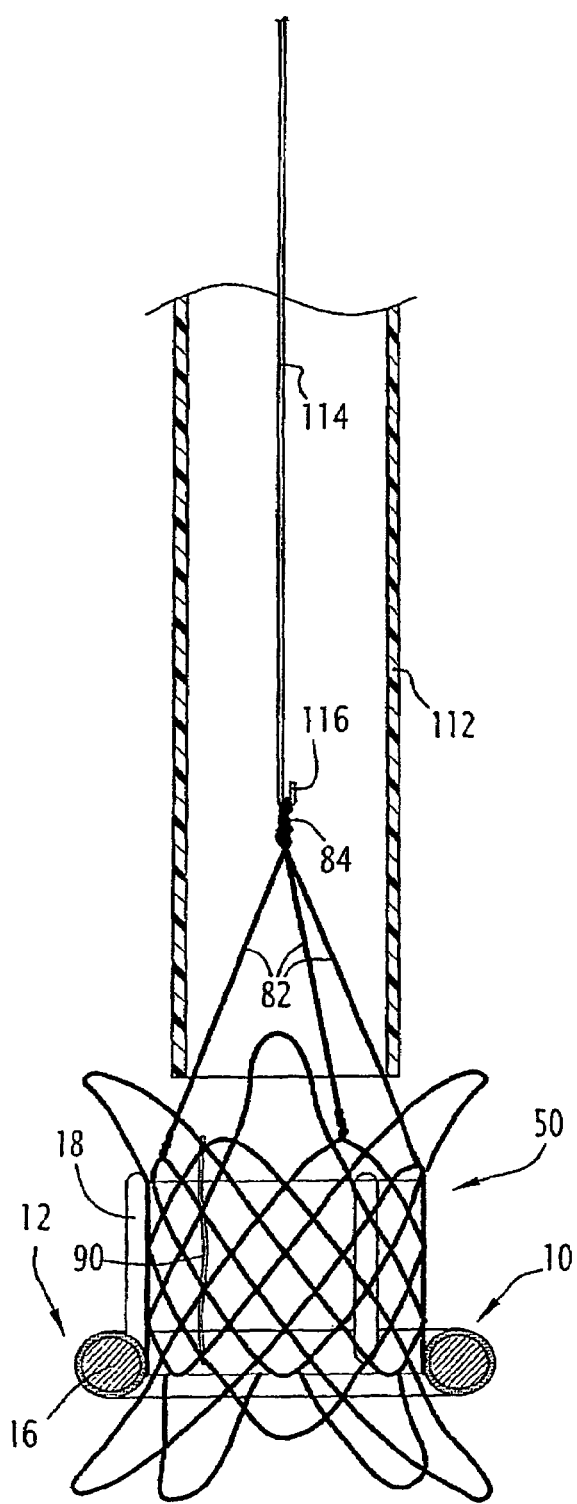
FIGS. 7 and 8 are views identical to those of FIGS. 5 and 6, showing successive stages in withdrawing a prosthetic valve from a valve prosthesis of the invention.
Figure 8:
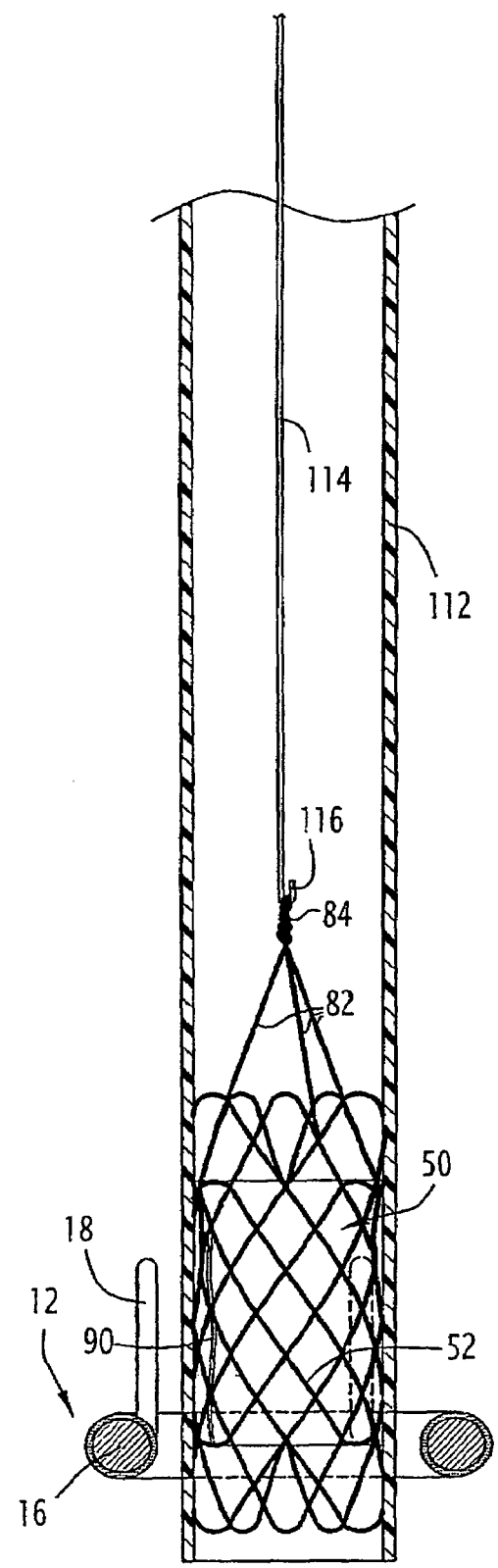

As shown in FIGS. 7 and 8, in order to withdraw a damaged prosthetic valve 50, a catheter 112 is introduced through the aorta and is placed facing the end of the valve that presents the tripod made up of the legs 82.

A traction tool 114 is conveyed along the catheter 112. At its end, the tool has a hook 116 suitable for catching the connection point 84 of the tripod. While the open end of the catheter is in contact with the legs 82 of the tripod, the prosthetic valve 50 is progressively introduced into the inside of the catheter 112 by advancing the catheter 112 along the length of the valve 50. By a camming effect, the legs 82 are pushed towards the axis and the prosthetic valve is progressively moved into its tight state and becomes inserted in the catheter 112, as shown in FIG. 8. The catheter 112 containing the prosthetic valve 50 is then extracted from the human body.

A new prosthetic valve 50 is then introduced using a kit 100 for performing treatment in the human body, and the new valve is deployed as explained above.

It will be understood that with such a vascular prosthesis, only one major surgical operation is required for putting the carrier structure 12 in place, after which the prosthetic valve can be changed periodically by an endoluminal approach, which constitutes an operation that is relatively minor for the patient.

The absence of any shutter-forming element on the carrier structure that has the sole function of providing a rigid bearing surface for the prosthetic valve, makes it possible to have a bearing surface that is satisfactory and clean regardless of the state of the prosthetic valve.

In contrast, when a prosthetic valve formed by a stent fitted with a shutter is implanted through a damaged prosthetic valve that comprises a carrier structure and a shutter, then the presence of the often-calcified shutter impedes putting the new prosthetic valve into place.

The invention claimed is:

1. A valve prosthesis comprising:
   a radially-rigid annular carrier structure to be surgically implanted at a location of a heart valve, said carrier structure comprising an annular support without any shutter for restricting a flow of blood to only one direction; and
   an interchangeable prosthetic valve independent of said carrier structure, said prosthetic valve being configured to be inserted through and positioned in said carrier structure by an endoluminal process, said prosthetic valve including:
      a tubular support radially deformable relative to a main axis, said tubular support including a tubular lattice covered in a liquid-proof stretchable film configured to define a solid liquid-proof cylindrical wall, said tubular support being deformable between a folded position in which said tubular support is to be inserted into said carrier structure, and a deployed position in which said tubular support is positioned within said carrier structure such that an outer periphery of said tubular support bears against said carrier structure; and
      a flexible shutter connected to said tubular support and deformable between an obstruction position in which said flexible shutter extends transversely with respect to said tubular support, and a release position in which said flexible shutter is contracted transversely with respect to said tubular support under action of the blood flowing through said tubular support;
      wherein said tubular support and said flexible shutter of said prosthetic valve are held within said carrier structure in the deployed position of said tubular support so as to be jointly and independently removable from and relative to said carrier structure by an endoluminal process.

2. The valve prosthesis of claim 1, further comprising a rigid member extending generally along a generator line of said tubular support, said rigid member being connected to said tubular support at least two points spaced apart along a longitudinal axis of said tubular support.

3. The valve prosthesis of claim 2, wherein said rigid member has a projecting end for connection to a prop for holding said prosthetic valve in position.

4. The valve prosthesis of claim 1, wherein said tubular support has a cylindrical middle trunk and a frustoconical collar at each axial end of said middle trunk, each of said frustoconical collars being configured to flare from said middle trunk towards ends of said tubular support.

5. The valve prosthesis of claim 1, wherein said tubular support is resilient and is shaped to be urged resiliently from said folded position towards said deployed position.

6. The valve prosthesis of claim 1, wherein said tubular support has a trunk and converging legs extending from said trunk so as to form a tripod, said converging legs each having a distal end connected together at a connection point lying substantially on a center longitudinal axis of said tubular support.

7. The valve prosthesis of claim 1, wherein said flexible shutter includes three membranes deformable between a closed position in which the free edges of the membranes touch one another in pairs over at least half their length, and an open position in which the three membranes are spaced apart from one another to allow blood to pass therethrough.

8. The valve prosthesis of claim 1, wherein said carrier structure includes a rigid ring and a set of rigid pegs each extending from said ring parallel to a center axis of said ring.

9. The valve prosthesis of claim 1, wherein said carrier structure includes a surface textile sheet to allow said carrier structure to be sutured to a body.

10. A treatment kit comprising:
    said valve prosthesis of claim 1; and
    a catheter for positioning said prosthetic valve in said carrier structure.

11. The valve prosthesis of claim 1, wherein said tubular support is configured to be held within said carrier structure in said deployed position without sutures or fasteners by a force of said outer periphery of said tubular support bearing against said carrier structure.

12. The valve prosthesis of claim 1, wherein said prosthetic valve is entirely independent of said carrier structure.

13. A valve prosthesis comprising:
    a radially-rigid annular carrier structure to be surgically implanted at a location of a heart valve, said carrier structure comprising an annular support without any shutter for restricting a flow of blood to only one direction; and
    an interchangeable prosthetic valve independent of said carrier structure to be inserted through and positioned in said carrier structure by an endoluminal process, said prosthetic valve including:
       a tubular support radially deformable relative to a main axis, said tubular support including a tubular lattice covered in a liquid-proof stretchable film configured to define a solid liquid-proof cylindrical wall, said tubular support having a cylindrical middle trunk and a frustoconical collar at each axial end of said middle trunk, each of said frustoconical collars being configured to flare from said middle trunk towards ends of said tubular support, said tubular support being deformable between a folded position in which said tubular support is inserted into said carrier structure, and a deployed position in which said tubular support is positioned within said carrier structure such that an outer periphery of said tubular support bears against said carrier structure; and
       a flexible shutter connected to said tubular support and deformable between an obstruction position in which said flexible shutter extends transversely with respect to said tubular support, and a release position in which said flexible shutter is contracted transversely with respect to said tubular support under action of the blood flowing through said tubular support.

14. A valve prosthesis comprising:

a radially-rigid annular carrier structure to be surgically implanted at a location of a heart valve, said carrier structure comprising an annular support without any shutter for restricting a flow of blood to only one direction, said carrier structure including a rigid ring and a set of rigid pegs each extending from said ring parallel to a center axis of said ring; and an interchangeable prosthetic valve independent of said carrier structure to be inserted through and positioned in said carrier structure by an endoluminal process, said prosthetic valve including:

a tubular support radially deformable relative to a main axis, said tubular support including a tubular lattice covered in a liquid-proof stretchable film configured to define a solid liquid-proof cylindrical wall, said tubular support being deformable between a folded position in which said tubular support is inserted into said carrier structure, and a deployed position in which said tubular support is positioned within said carrier structure such that an outer periphery of said tubular support bears against said carrier structure; and a flexible shutter connected to said tubular support and deformable between an obstruction position in which said flexible shutter extends transversely with respect to said tubular support, and a release position in which said flexible shutter is contracted transversely with respect to said tubular support under action of the blood flowing through said tubular support.

* * * * *